US00PP31509P2

(12) United States Plant Patent
Hofmann

(10) Patent No.: US PP31,509 P2
(45) Date of Patent: Mar. 3, 2020

(54) ***MANDEVILLA* PLANT NAMED 'INMANBOCHP'**

(50) Latin Name: *Mandevilla sanderi*
Varietal Denomination: Inmanbochp

(71) Applicant: Birgit Hofmann, Rudesheim am Rhein (DE)

(72) Inventor: Birgit Hofmann, Rudesheim am Rhein (DE)

(73) Assignee: Innovaplant Zierpflanzen GmbH & Co. KG, Gensingen (DE)

( * ) Notice: Subject to any disclaimer, the term of this patent is extended or adjusted under 35 U.S.C. 154(b) by 0 days.

(21) Appl. No.: 16/350,761

(22) Filed: Dec. 31, 2018

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./232, 226
CPC ... A01H 5/02; A01H 5/00; A01H 5/12; A01H 6/088; A01H 6/08
See application file for complete search history.

*Primary Examiner* — June Hwu
(74) *Attorney, Agent, or Firm* — C. A. Whealy

(57) ABSTRACT

A new and distinct cultivar of *Mandevilla* plant named 'Inmanbochp', characterized by its compact, upright and vining plant habit; low vigor to moderately vigorous growth habit; freely branching habit; moderately glossy dark green-colored leaves; freely flowering habit; red-colored flowers with yellow orange-colored centers; and relative tolerance to low temperatures.

2 Drawing Sheets

Botanical designation: *Mandevilla sanderi.*
Cultivar denomination: 'INMANBOCHP'.

BACKGROUND OF THE INVENTION

The present invention relates to a new and distinct cultivar of *Mandevilla* plant, botanically known as *Mandevilla sanderi* and hereinafter referred to by the name 'Inmanbochp'.

The new *Mandevilla* plant is a product of a planned breeding program conducted by the Inventor in Johannesburg, South Africa and Heidesheim, Germany. The objective of the breeding program is to create new freely branching *Mandevilla* plants that flower freely and have attractive flowers that resist fading and sun scald.

The new *Mandevilla* plant is a naturally-occurring whole plant mutation of *Mandevilla sanderi* 'Inmanbocre'. The new *Mandevilla* plant was discovered and selected by the Inventor as a single flowering plant from within a population of plants of 'Inmanbocre' in a controlled greenhouse environment in Heidesheim, Germany in August, 2016.

Asexual reproduction of the new *Mandevilla* plant by vegetative cuttings in a controlled greenhouse environment in Heidesheim, Germany since August, 2016 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Inmanbochp'. These characteristics in combination distinguish 'Inmanbochp' as a new and distinct *Mandevilla* plant:

1. Compact, upright and vining plant habit.
2. Low vigor to moderately vigorous growth habit.
3. Freely branching habit.
4. Moderately glossy dark green-colored leaves.
5. Freely flowering habit.
6. Red-colored flowers with yellow orange-colored centers.
7. Relatively tolerant to low temperatures.

Plants of the new *Mandevilla* can be compared to plants of the mutation parent, 'Inmanbocre'. Plants of the new *Mandevilla* differ, primarily from plants of 'Inmanbocre' in flower color as plants of the new *Mandevilla* have red-colored flowers with yellow orange-colored centers whereas plants of 'Inmanbocre' have darker red-colored flowers.

Plants of the new *Mandevilla* can be compared to plants of *Mandevilla sanderi* 'Inmanboclp', disclosed in a U.S. Plant patent application Ser. No. 16/350,760 filed concurrently. Plants of the new *Mandevilla* differ primarily from plants of 'Inmanboclp' in flower color as plants of the new *Mandevilla* have red-colored flowers with yellow orange-colored centers whereas plants of 'Inmanboclp' have light red purple-colored flowers with darker red purple-colored venation and yellow orange-colored centers.

Plants of the new *Mandevilla* can also be compared to plants of *Mandevilla sanderi* 'Lanarkansas', not patented. In side-by-side comparisons plants of the new *Mandevilla* differ primarily from plants 'Lanarkansas' in the following characteristics:

1. Plants of the new *Mandevilla* are smaller than plants of 'Lanarkansas'.
2. Plants of the new *Mandevilla* have smaller leaves than plants of 'Lanarkansas'.

3. Plants of the new *Mandevilla* have smaller flowers than plants of 'Lanarkansas'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'Inmanbochp' grown in a container.

The photograph on the second sheet is a close-up view of a typical flowering plant of 'Inmanbochp'.

DETAILED BOTANICAL DESCRIPTION

The aforementioned photographs and following observations, measurements and values describe plants grown during the spring and summer in 11-cm containers with wooden support frames in a glass-covered greenhouse in Heidesheim, Germany and under cultural practices typical of commercial *Mandevilla* production. During the production of the plants, day temperatures ranged from 20° C. to 40° C. and night temperatures ranged from 15° C. to 25° C. Plants were four months old when the photographs and description were taken. In the following description, color references are made to The Royal Horticultural Society Colour Chart, 2015 Edition, except where general terms of ordinary dictionary significance are used.

Botanical classification: *Mandevilla sanderi* 'Inmanbochp'.

Parentage: Naturally-occurring whole plant mutation of *Mandevilla sanderi* 'Inmanbocre'.

Propagation:

*Type.*—By vegetative cuttings.

*Time to initiate roots, summer.*—About three weeks at temperatures ranging from 20° C. to 35° C.

*Time to initiate roots, winter.*—About three weeks at temperatures ranging from 20° C. to 25° C.

*Time to produce a rooted young plant, summer.*—About 20 to 25 days at temperatures ranging from 20° C. to 35° C.

*Time to produce a rooted young plant, winter.*—About 25 to 30 days at temperatures ranging from 20° C. to 25° C.

*Root description.*—Thick, fleshy; typically white in color, actual color of the roots is dependent on substrate composition, water quality, fertilizers, substrate temperature and physiological age of roots.

*Rooting habit.*—Low branching; medium density.

Plant description:

*Plant and growth habit.*—Upright and vining plant habit; roughly oblong in overall shape; low vigor to moderately vigorous growth habit and low to moderate growth rate.

*Plant height, soil level to top of foliar plane.*—About 32.5 cm.

*Plant height, soil level to top of floral plane.*—About 34 cm.

*Plant diameter* (*spread*).—About 30 cm.

*Lateral branch description.*—Branching habit: Freely branching habit, primary lateral branches each with about five secondary lateral branches. Length: About 16.8 cm. Diameter: About 2 mm. Internode length: About 4.2 cm. Aspect: Primary lateral branches, about 10° from vertical; secondary lateral branches, about 40° from primary branch axis. Strength: Strong. Texture and luster: Smooth, glabrous; glossy; becoming woody with development. Color, developing: Close to 143B. Color, developed: Close to between 143B and 144A; when woody, close to 199C.

Leaf description:

*Arrangement.*—Opposite, simple.

*Length.*—About 7 cm.

*Width.*—About 4.6 cm.

*Shape.*—Elliptic to oblong.

*Apex.*—Short apiculate.

*Base.*—Truncate.

*Margin.*—Entire; not undulate.

*Texture and luster, upper surface.*—Smooth, glabrous; moderately coriaceous; moderately glossy.

*Texture and luster, lower surface.*—Smooth, glabrous; moderately coriaceous; slightly glossy.

*Venation pattern.*—Pinnate.

*Color.*—Developing leaves, upper , surface: Slightly darker than close to 137A and 143A. Developing leaves, lower surface: Close to between 143C and 144A. Full expanded leaves, upper surface: Close to between NN137A and 139A; venation, close to 144A. Fully expanded leaves, lower surface: Close to between 144A and 146B; venation, close to 145A to 145B.

*Petioles.*—Length: About 1.1 cm. Diameter: About 2 mm by 3 mm. Strength: Moderately strong. Texture and luster, upper surface: Smooth, glabrous; slightly glossy. Texture and luster, lower surface: Smooth, glabrous; moderately glossy. Color, upper surface: Close to 144A. Color, lower surface: Close to 144B.

Flower description:

*Flower type and flowering habit.*—Single salverform flowers arranged singly or in axillary cymes; flowers face mostly outwardly; freely flowering habit with about two flowers per inflorescence and about 42 flower buds and open flowers developing per plant.

*Natural flowering season.*—Plants flower continuously from spring into the autumn in Germany; plants begin flowering about ten weeks after propagation.

*Flower longevity on the plant.*—Individual flowers last about ten days; flowers not persistent.

*Fragrance.*—None detected.

*Inflorescence height.*—About 10.2 cm.

*Inflorescence diameter.*—About 11.8 cm.

*Flower buds.*—Length: About 6.1 cm. Diameter: About 1 cm. Shape: Narrowly oblanceolate. Texture and luster: Smooth, glabrous; slightly glossy. Color: Distally, close to 53D; proximally, close to 145C; at the base, close to 145A.

*Flowers.*—Appearance: Flared trumpet, corolla fused and five-parted. Diameter: About 8.5 cm. Depth (length): About 7.9 cm. Throat diameter: About 1.4 cm. Tube length: About 4.9 cm. Tube diameter: Proximally, about 4 mm; distally, about 1.5 cm.

*Corolla.*—Quantity and arrangement: Five petals arranged in a single whorl; lower 53.5% portion of the petals are fused into a funnelform tube. Petal length: About 8.6 cm. Petal width: About 3.2 cm. Petal shape and appearance: Roughly spatulate. Petal apex: Apiculate. Petal margin: Entire; moderately undulate. Petal texture and luster, upper surface: Smooth, glabrous; moderately velvety; matte. Petal texture and luster, lower surface: Smooth, glabrous; slightly velvety; very slightly glossy. Throat texture: Smooth, glabrous; moderately velvety. Tube texture: Smooth, glabrous; slightly velvety. Color: Petal, when opening, upper surface: Close to 53C to 53D; at the throat, close to 46B. Petal, when opening, lower surface: Close to 54A to 54C. Petal, fully opened, upper surface: Close to 53B to 53C; towards the margins, close to 54A; at the throat, close to N45C; venation, similar to lamina; color does not change with development. Petal, fully opened, lower surface: Close to 54A; venation, similar to lamina; color does not change with development. Throat: Close to 15A; proximally, close to 150B to 150C; venation, similar to lamina. Tube: Close to 145C to 145D; proximally, close to 145A; axillary stripes, close to 54B; venation, similar to lamina.

*Calyx.*—Quantity and arrangement: Five sepals arranged in a single whorl. Calyx length: About 9 mm. Calyx diameter: About 4.5 mm. Sepal length: About 8 mm. Sepal width: About 2 mm. Sepal shape: Lanceolate. Sepal apex: Narrowly acuminate. Sepal base: Broadly cuneate. Sepal margin: Entire. Sepal texture and luster, upper surface: Smooth, glabrous; moderately glossy. Sepal texture and luster, lower surface: Smooth, glabrous; slightly glossy. Sepal color: When developing and fully developed, upper surface: Close to 145B; at the apex, close to 145A. When developing and fully developed, lower surface: Close to 145B.

*Peduncles.*—Length: About 5.5 cm. Diameter: About 2 mm. Strength: Strong. Aspect: About 25° from lateral branch axis. Texture and luster: Smooth, glabrous; glossy. Color: Close to 143A.

*Pedicels.*—Length: About 1.6 cm. Diameter: About 2 mm. Strength: Strong. Aspect: About 35° from peduncle axis. Texture and luster: Smooth, glabrous; glossy. Color: Close to 144B to 144C.

*Reproductive organs.*—Stamens: Quantity and arrangement: Typically five; basifixed; anthers connivent. Filament length: About 1.5 mm. Filament color: Close to 151D. Anther shape: Narrowly oblong. Anther size: About 1 cm by 1.5 mm. Anther color: Close to 161C. Pollen amount: None observed. Pistils: Quantity: Typically one. Pistil length: About 2.3 cm. Style length: About 2 cm. Style color: Close to 145D. Stigma diameter: About 2 mm. Stigma shape: Club-shaped, pointed. Stigma color: Close to 152D. Ovary color: Close to 144A.

*Seeds and fruits.*—To date, seed and fruit production have not been observed on plants of the new *Mandevilla.*

Pathogen & pest resistance: To date, plants of the new *Mandevilla* have not been noted to be resistant to pathogens and pests common to *Mandevilla* plants.

Temperature tolerance: Plants of the new *Mandevilla* have been observed to tolerate temperatures ranging from about 5° C. to about 40° C. and to be suitable for USDA Hardiness Zones 9 to 13.

It is claimed:

1. A new and distinct *Mandevilla* plant named 'Inmanbochp' as illustrated and described.

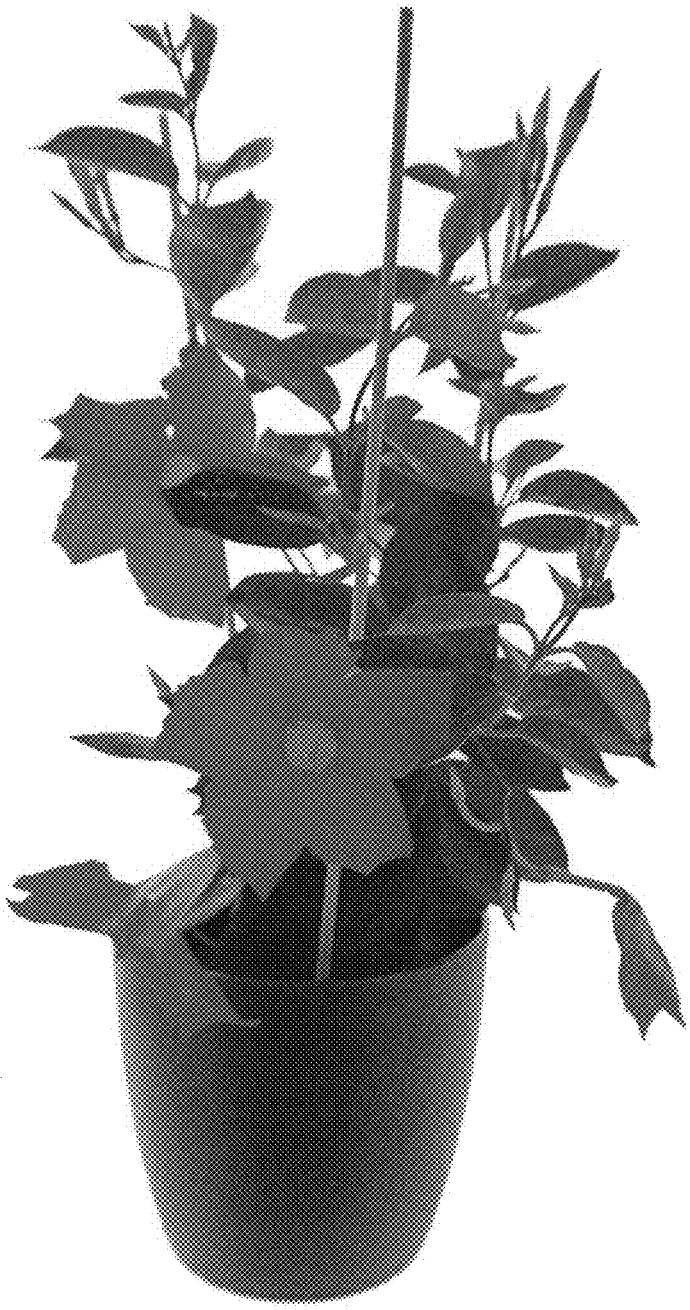

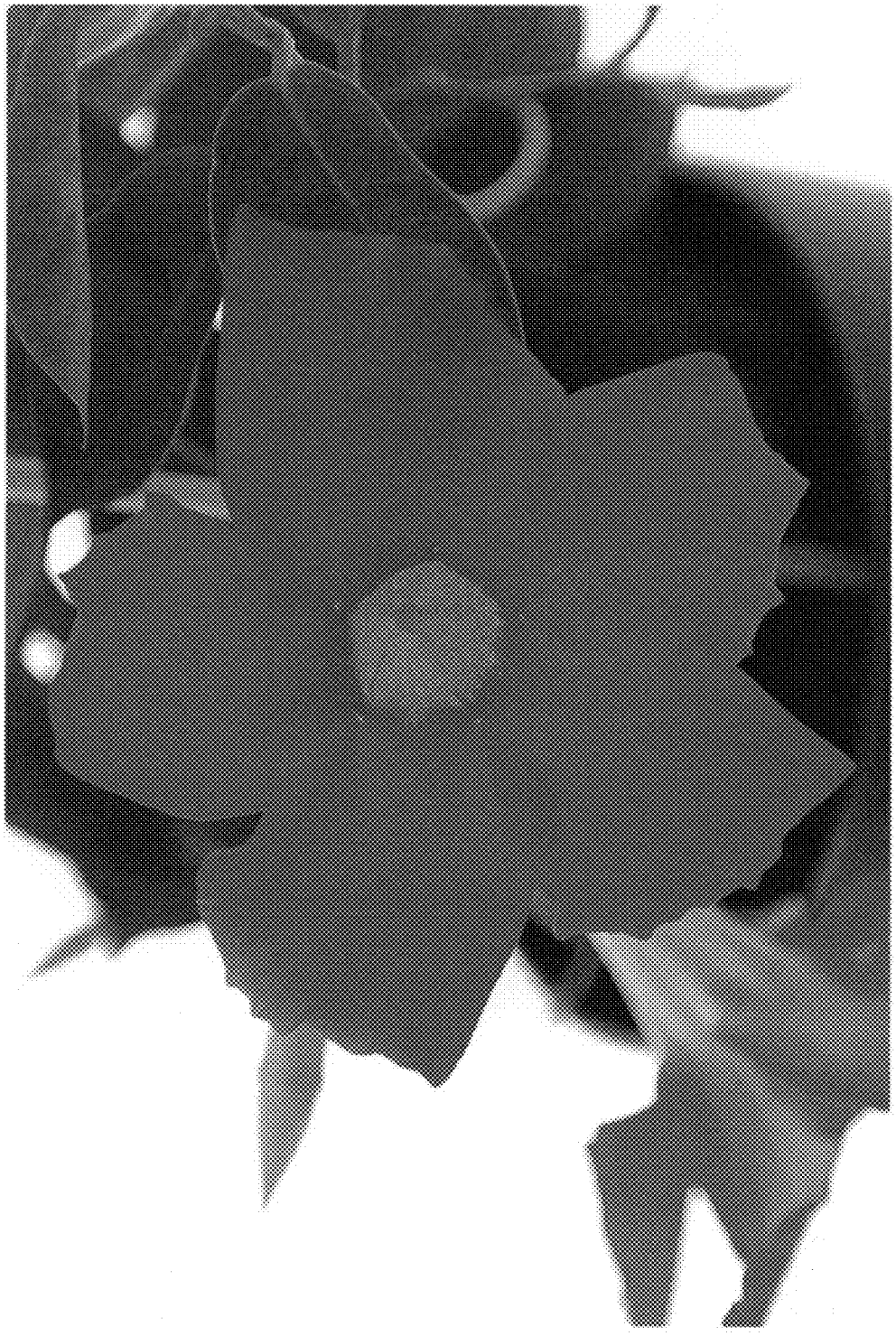

* * * * *